United States Patent [19]
Sørensen et al.

[11] Patent Number: 6,136,578
[45] Date of Patent: Oct. 24, 2000

[54] STORAGE-STABLE LIQUID FORMULATION COMPRISING A LACCASE

[75] Inventors: Niels Henrik Sørensen, Skævinge; Grethe Rasmussen, Farum; Lotte Rugholm Henriksen, Vanløse, all of Denmark

[73] Assignee: Novo Nordisk A/S, Bagsværd, Denmark

[21] Appl. No.: 09/037,817

[22] Filed: Mar. 10, 1998

[30] Foreign Application Priority Data

Mar. 12, 1997 [DK] Denmark ................................ 0269/97
Apr. 1, 1997 [DK] Denmark ................................ 0366/97

[51] Int. Cl.$^7$ ........................................................ C12N 9/96
[52] U.S. Cl. ........................ 435/188; 435/189; 435/190; 435/191
[58] Field of Search ................................. 435/190, 191, 435/189, 188

[56] References Cited

FOREIGN PATENT DOCUMENTS

| | | |
|---|---|---|
| 2 235 135 | 1/1975 | France . |
| 1 323 819 | 5/1971 | United Kingdom . |
| WO 95/01426 | 12/1995 | WIPO . |

OTHER PUBLICATIONS

Derwent accession No. 96–203142—Abstract of JP 8070861 (1996).
Derwent accession No. 97–206626—Abstract of JP 9056378 (1997).
Dialog accession No. 16392003—Abstract of Biotechnology Techniques 12 (2):101–104 (1998).
Taiyo Kagaku K.K., Patent Abstract of Japan, vol. 11, No. 222, (Feb. 17, 1987).
Nippon Shinyaku Co. LTD., Patent Abstract of Japan, vol. 10, No. 335, (Jun. 26, 1996).
Biochimica et Biophysica Acta, vol. 1292, pp. 303–311 (1996).
Appl. Microbiol Biotechnol, vol. 39, pp. 632–636 (1993).

*Primary Examiner*—Francisco Prats
*Attorney, Agent, or Firm*—Steve T. Zelson, Esq.; Reza Green, Esq.

[57] ABSTRACT

The present invention relates to a storage-stable liquid formulation comprising a laccase comprising (i) a laccase, (ii) at least one polyalcohol, which formulation has a pH which is more alkaline than the pH optimum of the laccase. It is also an object of the invention to provide a method for improving the storage-stability of liquid formulations comprising a laccase and the use of said liquid formulations for a personal care application or for bleaching or for textile applications such as dyeing of fabrics.

24 Claims, 6 Drawing Sheets

STORAGE-STABLE LIQUID FORMULATION COMPRISING A LACCASE

CROSS-REFERENCE TO RELATED APPLICATIONS

This application claims priority under 35 U.S.C. 119 of Danish application 0269/97 filed Mar. 12, 1997 and 0366/97 filed Apr. 1, 1997, the contents of which are fully incorporated herein by reference.

FIELD OF THE INVENTION

The present invention relates to a storage-stable liquid formulation comprising a laccase, a method for improving the storage-stability of liquid formulations comprising a laccase and the use of said liquid formulations for a personal care application or for bleaching or for textile applications such as dyeing of fabrics.

BACKGROUND OF THE INVENTION

Industrial enzymes have generally been formulated as particulate solids (e.g. in powder or granulated form, optionally with a coating of some kind) or in the form of a water-based solution.

A number of solid formulations (e.g. enzyme powders) have the disadvantage that dust formation readily takes place, which—unless special precautions are taken may result in contamination of the surrounding environment and thereby pose a risk to the health of persons handling such compositions.

Water-based, liquid enzyme formulations essentially eliminate the risk of dust formation. owing to the fact that practically all enzymes exert their activity in the presence of water it is generally not feasible to prepare storage-stable formulations comprising free (e.g. unencapsulated or uncoated) enzymes.

Currently available water-based liquid enzyme formulations have a relatively short time span, within which it is possible to operate, as the residual enzymatic activity is reduced to an unacceptable low level after a few weeks of storage if not stored under cooling.

Feng Xu et al, (1996), Biochimica et Biophysica Acta, 1292, p. 303–311 shows that the stability of various laccases is dependent on the pH and the temperature after pre-incubation with ABTS for 1 hour.

Palmiert et al., (1993), Applied Microbiol. Biotechnol., 39, p. 632–636, shows that a specific laccase incubated at 25° C. is more stable at pH 7 than at pH 3 for a period of 300 minutes (i.e. 6 hours).

Thus, there is a need for liquid formulations comprising a laccase which are storage-stable for a period of more than one day. The present invention provides formulations fulfilling such a need.

SUMMARY OF THE INVENTION

It is the object of the present invention to provide a storage-stable liquid formulation comprising a laccase which is storage-stable at 10–60° C. for a prolonged period of time.

A liquid formulation comprising (i) a laccase and (ii) at least one polyalcohol, which formulation has a pH which is more alkaline than the pH optimum of the laccase, has an improved storage stability or shelf-life in comparison to corresponding formulation without (a) polyalcohol(s) with a pH at the pH optimum of the laccase in question.

Laccases

Laccases (benzenediol:oxygen oxidoreductases) (E.C. class 1.10.3.2 according to Enzyme Nomenclature (1992) Academic Press, Inc.) are multi-copper containing enzymes that catalyse the oxidation of phenols. Laccase-mediated oxidation results in the production of aryloxy-radical intermediates from suitable phenolic substrates; the ultimate coupling of the intermediates so produced provides a combination of dimeric, oligomeric, and polymeric reaction products. Certain reaction products may be used to form dyes suitable for dyeing keratinous fibres, such as hair, wool and textiles. Laccases are obtainable from a variety of microbial sources, notably bacteria and fungi (including filamentous fungi and yeasts), and suitable examples of laccases are to found among those obtainable from fungi, including laccases obtainable from strains of Aspergillus, Neurospora (e.g. *N. crassa*), Podospora, Botrytis, Collybia, Fomes, Lentinus, Pleurotus, Trametes [some species/strains of which are known by various names and/or have previously been classified within other genera; e.g. *Trametes villosa*=*T. pinsitus*=*Polyporus pinsitis* (also known as *P. pinsitus* or *P. villosus*)=*Coriolus pinsitus*], Polyporus, Rhizoctonia (e.g. *R. solani*), Coprinus (e.g. *C. plicatilis, Coprinus cinereus*), Psatyrella, Myceliophthora (e.g. *M. thermophila*), Schytalidium, Phlebia (e.g. *P. radita*; see WO 92/01046), Coriolus (e.g. *C. hirsutus*; see JP 2-238885), Pyricularia or Rigidoporus.

Preferred laccases in the context of the invention include laccases obtainable from *Myceliophthora thermophila* and laccase obtainable from *Polyporus pinsitus*.

A liquid formulation of the invention may or may not contain other ingredients. Other ingredients contemplated include laccase substrate or mediator, pH regulating agents, anti-microbial agents, dispersing agents and/or viscosity-regulating agents.

The invention also relates to a method for improving the storage-stability of a laccase by storing the laccase in the presence of a polyalcohol at a pH, which is 0.5 to 5.5 pH units more alkaline than the pH optimum of the laccase.

Finally the invention relates to the use of a liquid formulation of the invention for personal care applications, such as for hair dying, bleaching and for textile application such as dyeing of fabrics.

DETAILED DESCRIPTION OF THE INVENTION

Figure 1:
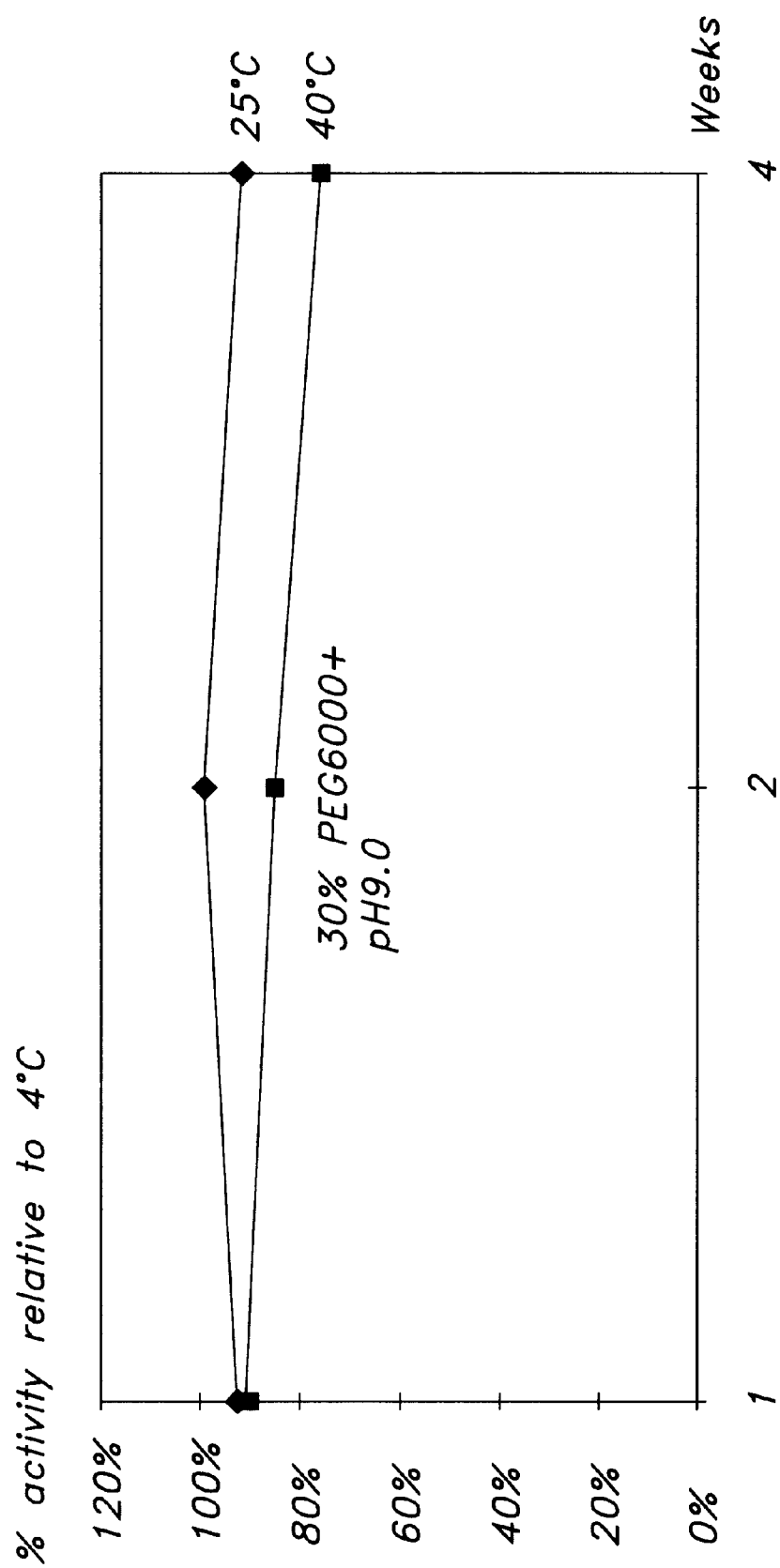
FIG. 1 shows the relative residual enzymatic activity of a liquid formulation of the invention comprising *Myceliophtora thermophila* laccase (120 LAMU/g) and 30% PEG6,000 at pH 9.0 vs. storage period in weeks.

The object of the present invention is to provide a liquid formulation comprising a laccase with improved storage-stability, which formulation maintains a substantially percentage of residual enzyme activity when stored at a temperature from 10–60° C., preferably 20–45° C.

The inventors have found that a liquid formulation comprising a laccase and a polyalcohol which formulation has a pH which is more alkaline than the pH optimum of the laccase, has improved storage-stability or shelf life.

To obtain an improved storage-stable liquid formulation, having a prolonged shelf-life in the range of more than one day to several weeks and even in certain cases up to several months, the pH must be from 0.5 to 5.5 pH units, typically from 1 to 4 pH units more alkaline than the pH optimum of the laccase in question.

An "improved storage-stable liquid formulation", is at least in the context of the present invention, determined on the basis of the percentage of residual enzymatic activity of the laccase in question after a period of time at a fixed pH in comparison to the enzymatic activity after the same period of time at the same fix pH under cooling at 4° C. Cooling at 4° C. is the conventional way of storing a liquid formulation comprising a laccase, such as a *Myceliophthora thermophila* laccase.

A "substantial residual enzymatic activity" means a maintained enzymatic activity which is at least 20%, better more than 30%, such as more than 50% or 60%, even better more than 70%, preferably more than 80%, especially more that 90% and even up to 100% of the enzymatic activity of the laccase in question stored at 40° C. under corresponding conditions.

pH

The pH of the liquid formulation of the invention—which is more alkaline than the pH optimum of the laccase in question—may be the "natural" pH resulting from the formulation's ingredients. If the "natural" pH of the liquid formulation is not in accordance with the instructions of the present invention the pH must be adjusted to a desired pH by the use of a pH regulating agent e.g. a buffer. It is to be understood that what pH the liquid formulation specifically must have is dependent on the specific laccase as the pH optimum of laccases differs from 4 to 8.

The pH optimum of a specific laccase is dependent on the presence of substrates, stabilizers (i.e. in the present case the polyalcohol), the buffers and other ingredients. Therefore the pH optimum of the laccase must be measured in a formulation corresponding to the formulation in which it is to be stored. A person skilled in the art can easily determine the pH optimum of the laccase in question and from that information easily prepare a storage-stable liquid formulation of the invention.

Laccase

The laccases in question may be any laccase as described above. Laccases are obtainable from quite different sources and are a relatively heterogeneous group with respect to their structure (molecular weight, composition) and their properties (specificity with respect to the substrate, optimum pH, isoelectric point (pI) etc.).

Examples of laccases specifically contemplated according to the invention include laccases of plant origin, such as a Rhus sp. laccase from the lacquer tree, and laccases of microbial origin, including bacterial and fungal laccases, such as a *Rhizoctonia practicola* laccase (Reinhammar, B. B. A, 205, 35–47 (1970); Bollag et al. (1978), Can. J. Microbiol, 25, 229–233), a laccase derived from Myceliopthora, in particular a strain of *Myceliophtora thermophila* (see WO 95/33836), a laccase derived from Polyporus, in particular a strain of *Polyporus pinsitus* (see WO 96/00290), a laccase derived from Scytalidium sp., in particular *S. thermophilum* (See WO 95/33837), a laccase derived from Pyricolaria sp., in particular *P. oryzae*, a laccase derived from *Coprinus cinereus*.

The Concentration of Laccase in the Liquid Formulation of the Invention

The concentration of laccase in a liquid formulation of the invention depends on its intended application and may therefore differ from low concentrations to high concentrations. A person skilled in the art of the application in question (e.g. hair dyeing, fabric bleaching, fabric dyeing etc.), knows which final concentration of laccase is needed. Technically seen the improved storage-stability or shelf-life of the liquid formulation of the invention is obtained independently of the concentration of laccase, at least in concentrations from 1 mg enzyme protein per ml product and up to concentration where the viscosity gets so high that the mixing of the product is impossible.

*Myceliophthora thermophila* Laccase Formulation

The pH optimum of recombinant *Myceliophthora thermophila* laccase is according to WO 95/33836 (from Novo Nordisk) 6.5 using syringaldazin as substrate. Consequently, in the case of a formulation comprising said laccase the pH should according to the invention be more alkaline than 6.5 in the presence of a Tris-buffer, and should preferably lie in the range from 7 to 12, especially from 7.5 to 11.

*Myceliophthora thermophila* laccase in 10% mono propylene glycol (MPG), 0.2% Proxel™ in 0.25 M Glycine buffer at pH 9.0 maintains 84% enzymatic activity after 4 weeks at 40° C. At pH 9.0 the percentage residual activity was found to be higher than at pH 9.5.

Figure 4:
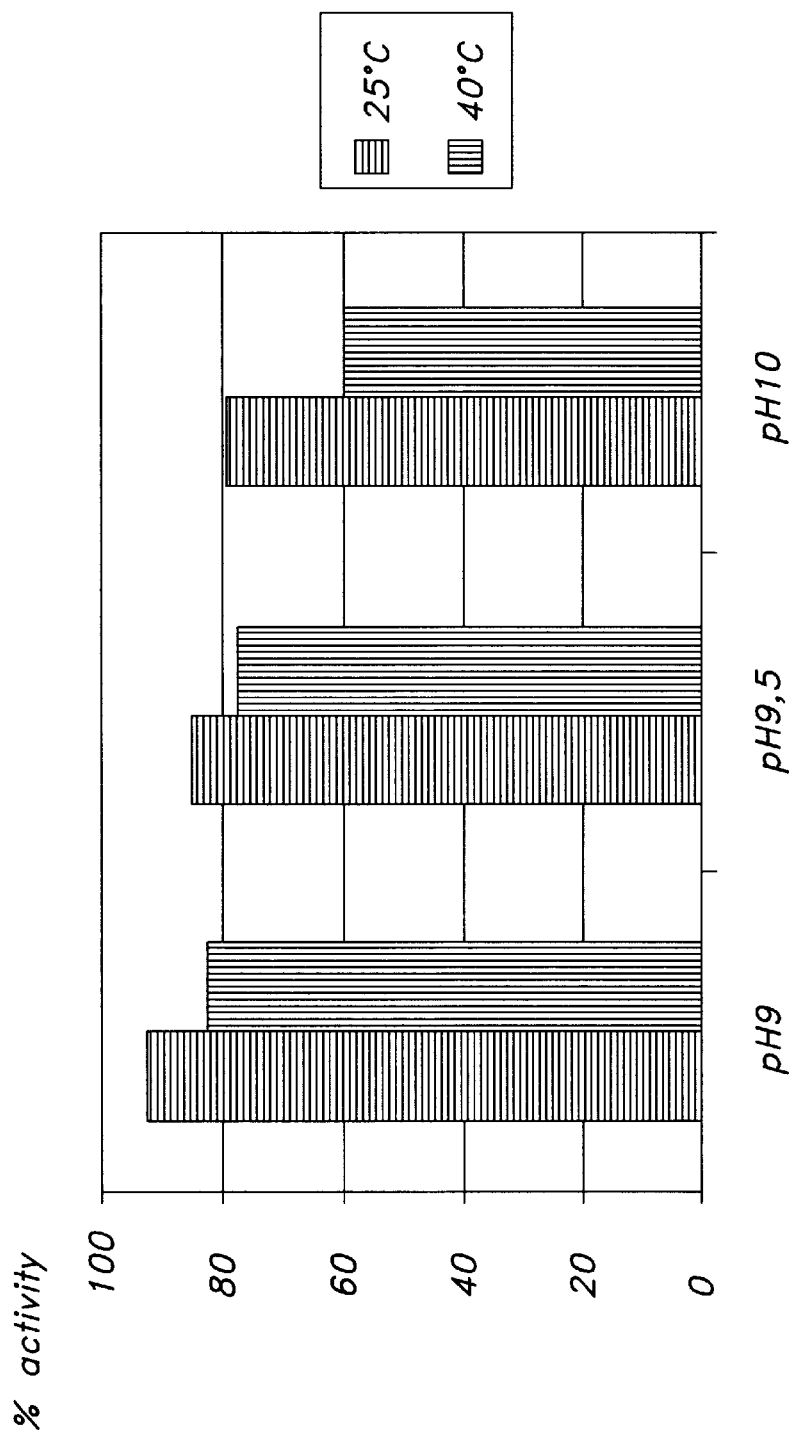
FIG. 4 shows the residual activity of *Myceliophthora thermophila* laccase at pH 9, 9.5 and 10.

The effect of increasing the pH from pH 9 to pH 10 is described in Example 5 and shown in FIG. 4. *Myceliophthora thermophila* laccase seems to be more stable at pH 9.0, where 93% and 84% activity is maintained after 4 weeks storage at 25° C. and 40° C. respectively.

*Polyporus pinsitus* Laccase Formulation

Further, recombinant *Polyporus pinsitus laccase has a pH optimum from* 5 to 5.5 using syringaldazin as substrate as disclosed in WO 96/00290 (Novo Nordisk).

According to the invention the pH in a liquid formulation comprising a laccase derived from *Polyporus pinsitus* and a polyalcohol should be more alkaline than 5 or 5.5 and should preferably lies from about 5.5 to 11, especially 6 to 9.5.

*Polyporus pinsitus* laccase in a liquid 60% PEG6,000 pH 9.0 had 100% residual activity after 14 days and 65% residual activity after 4 weeks at 40° C. as shown in Example 1.

The Polyalcohol

To obtain an improved storage-stability of liquid formulations comprising a laccase at least one polyalcohol must be present to stabilize the formulation.

Without being limited to any theory it is believed that the polyalcohol reduces the water activity and further ensures that the laccase does not precipitate and is not subject to thermal denaturation.

The inventors have found that polymers and monomers thereof, and mono-, di-, oligo- or polysaccharides are suitable polyalcohols to obtain the desired stabilization of the formulation.

Examples of polyalcohols which may be used in the liquid formulation of the invention include polyalkylene oxides (PAO), such as a polyalkylene glycols (PAG), including polymethylene glycols, polyethylene glycols (PEG), methoxypolyethylene glycols (mPEG) and polypropylen glycols, poly-vinyl alcohol (PVA), polyethylene-co-maleic acid anhydride, polystyrene-co-malic acid anhydrid, dextrans including carboxymethyl-dextrans, celluloses, including methylcellulose, carboxymethylcellulose, ethylcellulose, hydroxyethylcellulose carboxyethylcellulose and hydroxypropylcellulose, hydrolysates of chitosan, starches such as hydroxyethyl-straches and hydroxy propyl-starches, glycogen, agaroses and derivates thereof, guar gum, pullulan, inulin, xanthan gum, carrageenan, pectin, alginic acid hydrolysates, bio-polymers, sorbitol, glucose, mannose, galactose, arabinose, gulose, xylose, threose, sorbose, fructose, glycerol, maltose cellobiose, sucrose, amylose, amylopectin, mono propylene glycol (MPG).

In a preferred embodiment the formulation comprises a polymer and/or a saccharide as the polyalcohol(s). Suitable polymer(s) are polyalkylene oxide (PAO), preferably a polyalkylene glycol (PAG), especially propylene glycol. A preferred saccharide is glucose.

In an embodiment of the invention the polyalcohol has a molecular weight in the range from 100 da to 8,000 da, preferably 200 to 7,000 da, such as 6,000 and may constitute from 5 to 75%, preferably 10 to 60% especially 20 to 50% of the liquid formulation of the invention.

In an embodiment of the invention the liquid formulation is a water-based formulation. The laccase may be present in liquid form or in solid (amorphous and/or crystalline) generally particulate form, e.g. dispersed in the liquid phase (i.e. a slurry).

Further Ingredients

A liquid formulation of the invention may or may not comprise a laccase substrate or mediator.

In an embodiment the liquid formulation of the invention further comprises a laccase substrate or mediator, such as a dye precursor (in the case where the final product is a dyeing composition or product). This requires that the formulation is oxygen exhausted and that the pH is within the specified range above the pH optimum of the laccase in question.

Further ingredients include anti-microbial agents, pH-regulating agents, dispersing agents, viscosity-regulating agents and/or antioxidants.

Anti-microbial Agents:

Anti-microbial agents are materials which inhibit or prevent growth of microorganisms, such as bacteria, fungal organisms, such as filamentous fungi and/or yeasts. Suitable anti-microbial agent include sodium benzoates, potassium sorbate, nipagin, parabens etc. Proxel™ is the tradename of a suitable anti-microbial agent.

Dispersing Agents:

Dispersing agents (i.e. materials which help to prevent or delay separation (e.g. precipitation) of dispersed solid substances) include, e.g., certain finely divided clays (such as kaolin (china clay), bentonite, fuller's earth and the like), so-called "deflocculating polymers", as well as amphipathic materials of the anionic polymer type.

Viscosity-regulating Agents:

Examples of materials suitable for increasing the viscosity of embodiments of compositions of the invention include various grades of fumed silica (sold, e.g., under tradenames such as Aerosil™, Cab-O-Sil™ or Tix-O-Sil™), bentonite, kaolin, finely divided calcium carbonate, organo-clays (e.g. Claytone®), and polymeric materials such as hydroxypropylcellulose (e.g. Natrosol™) and xanthan gums.

pH-regulating Agents:

Examples of pH-regulating agents suitable for incorporation in some embodiments of a composition of the invention (i. e. substances which, when the composition of the invention is brought into contact with an aqueous medium, aid in adjusting and/or maintaining (i.e. buffering) the pH of the medium so as to provide a pH value which is compatible with pH-sensitive components of the formulation (such as a laccase present therein)) include various anhydrous inorganic and organic salts, such as potassium dihydrogen phosphate ($KH_2PO_4$), sodium hydrogen carbonate ($NaHCO_3$), potassium acetate ($CH_3COOK$), sodium acetate ($CH_3COONa$) and potassium dihydrogen citrate, Glycine buffer, Tris-Na-buffer.

Antioxidants:

With certain embodiments of formulation of the invention, it may be advantageous to incorporate, in the formulation, a substance (an antioxidant) which can protect an oxidation-sensitive component of the formulation against oxidation (e.g. by atmospheric oxygen). Such substances include, for example, salts as well as organic antioxidants such as Methionine and Lecithins.

Preparation of a Liquid Formulation of the Invention

With regard to the preparation of a liquid formulation of the invention, a number of approaches are applicable, depending mainly on the form in which the laccase to be incorporated therein are initially available.

In the case of the laccase is available in the form of a solid enzyme preparation being insoluble, such as a lyophilized or spray-dried micro-granulate, or are at least of low solubility in the liquid it may simply be dispersed in water to form a water-based liquid phase to form a slurry.

In cases where the laccase is available as an aqueous solution, it may be used directly in the liquid formulation of the invention.

Laccase Substrates

The term "substrate" as employed in the context of the present invention refers to a substance which is a reactant in a reaction catalyzed by the enzyme.

When it is appropriate to incorporate a laccase substrate in a formulation of the invention, the nature of the enzyme substrate suitable for this purpose will depend, not only on the laccase in question, but also on the intended application of the formulation.

(i) Mediators:

In an embodiments of the invention the liquid formulation comprises a laccase together with an oxidizable substrate therefore which functions as a mediator. The mediator can be any mediator appropriate for use with a laccase employed. Examples of mediators include the following: halide ions (e.g. chloride and bromide); certain metal ions (e.g. $Mn^{2+}$); phenolic species [e.g. acetosyringone, syringaldehyde, syringic acid, alkyl syringates (such as methyl, ethyl, propyl, butyl, hexyl or octyl syringate) and other syringic acid esters [e.g. syringate esters of polyethylene glycols (PEG's) of various molecular weights, such as a PEG4,000 syringate], ethyl 3-(4-hydroxy-3,5-dimethoxyphenyl)acrylate, p-hydroxycinnamic acid, 2,4-dichlorophenol, vanillin, 7-hydroxycoumarin, 6-hydroxy-2-naphthoic acid, and p-hydroxybenzene-sulfonate]; 2,2'-azino-bis(3-ethylbenzothiazoline-6-sulfonate) (ABTS; see, e.g., WO 94/12620); and 10-methyl-, 10-ethyl- and 10-propylphenothiazine (see, e.g., WO 94/12621). Other suitable mediators are disclosed in, e.g., WO 94/12619, WO 94/12620 and WO 94/12621.

Mediators of the syringate, phenoxazine or phenothiazine type are generally very suitable in the context of the invention, and some examples hereof are acetosyringone, methyl syringate, 10-phenothiazinepropionic acid, 10-ethylphenothiazine-4-carboxylic-acid, 10-phenoxazinepropionic acid and 10-methylphenoxazine (described in WO 94/12621).

Mediator will generally be present in a composition of the invention in an amount of from to $10^{-7}$ to $10^{-2}$ mol/g of composition, and often in an amount of from $10^{-5}$ to $10^{-3}$ mol/g of composition.

(ii) Dye Precursors:

Further important embodiments of a formulation of the invention are formulations comprising a laccase, such as one of the laccases mentioned above) together with one or more oxidizable substrates therefor in the form of dye precursor(s) which in the presence of water undergo(es) laccase-catalyzed oxidation (in general oxidative radical formation) and subsequently polymerize(s) to form a dye of a particular color. Such laccase-mediated dye formation has important industrial applications in the dyeing of textiles (e.g. wool, cotton and/or synthetics), yarn, fur, hides and the like, and in the field of human personal care, where it has been found to be well suited for use, e.g., in dyeing hair.

As used in the present specification and claims, the term "dye precursor" is intended to embrace not only an individual substance which upon oxidation in the presence of a laccase gives rise to a strongly colored dye, but also an individual substance which upon oxidation in a corresponding manner does not itself, alone, give rise to a product having a strong color, but which when subjected to oxidation in the presence of a substance in the former category of strongly coloring substances leads to a modification of the dye color which results. Oxidizable substances which exert such a modifying effect on the overall dye color (such substances sometimes being referred to as "modifiers") are thus included within the meaning of the term "dye precursor" as employed in the context of the invention.

Examples of dye precursors suitable for incorporation in a formulation of the invention include, but are not limited to: aromatic diamines; di-amino-substituted aromatic carboxylic acids and esters thereof; aminophenols; phenols; naphthols; and phenolic derivatives of cinnamic acids and esters thereof.

Examples of aromatic diamines include:
2-methyl-1,4-diaminobenzene,
4-methyl-o-phenylenediamine,
1,4-diamino-benzene (p-phenylenediamine),
2-methoxy-p-phenylenediamine,
2-methyl-1,4-diamino-benzene (p-toluylenediamine),
2-chloro-1,4-diamino-benzene (o-chloro-p-phenylenediamine),
4-amino diphenylamine (N-phenyl-p-phenylenediamine),
1-amino-4-β-methoxyethylamino-benzene(N-β-methoxyethyl p-phenylenediamine),
1-amino-4-bis-(β-hydroxyethyl)-aminobenzene (N,N-bis-(β-hydroxyethyl)-p-phenylenediamine),
1,3-diamino-benzene (m-phenylenediamine),
2-methyl-1,3-diamino-benzene (2,6-diaminotoluene),
2,4-diaminotoluene, and
2,6-diaminopyridine.

Examples of di-amino-substituted aromatic carboxylic acids and esters thereof include:
2,3-diaminobenzoic acid,
3,4-diaminobenzoic acid,
and esters, e.g. lower alkyl esters (such as methyl, ethyl, propyl, 2-propyl or butyl esters), of these Examples of aminophenols include:
1-hydroxy-2-amino-benzene (o-aminophenol),
1-hydroxy-3-amino-benzene (m-aminophenol),
1-methyl-2-hydroxy-4-amino-benzene (3-amino o-cresol),
1-methyl-2-hydroxy-4-β-hydroxyethylamino-benzene (2-hydroxy-4-β-hydroxyethylamino-toluene),
1-hydroxy-4-amino-benzene (p-aminophenol),
1-hydroxy-4-methylamino-benzene (p-methylaminophenol),
1-methoxy-2,4-diamino-benzene (2,4-diaminoanisole),
1-ethoxy-2,3-diamono-benzene (2,4-diaminophenetole), and
1-β-hydroxyethyloxy-2,4-diamino-benzene (2,4-diaminophenoxyethanol).

Examples of phenols and naphthols include:
1,2-dihydroxybenzene (pyrocatechol),
1,3-dihydroxybenzene (resorcinol),
1,3-dihydroxy-2-methylbenzene (2-methyl resorcinol),
1,3-dihydroxy-4-chlorobenzene (4-chloro resorcinol),
1,2,3-trihydroxybenzene (pyrogallol),
1,2,4-trihydroxybenzene,
1,2,4-trihydroxy-5-methylbenzene (2,4,5-trihydroxytoluene),
1,2,4-trihydroxytoluene,
1,5-dihydroxynaphthalene,
1,4-dihydroxybenzene (hydroquinone), and
1-hydroxynaphthalene (α-naphthol).

Examples of phenolic derivatives of cinnamic acids and esters thereof include: p-coumaric acid (i.e. 4-hydroxycinnamic acid), caffeic acid (i.e. 3,4-dihydroxycinnamic acid), sinapinic acid (sinapic acid; i.e. 3,5-dimethoxy-4-hydroxycinnamic acid), ferulic acid (i.e. 4-hydroxy-3-methoxycinnamic acid), and esters, e.g. lower alkyl esters (such as methyl, ethyl, propyl, 2-propyl or butyl esters), of any of these.

Other substances of interest as dye precursors in the context of the invention include salicylic acid (i.e. 2-hydroxybenzoic acid) and esters (e.g. lower alkyl esters, such as methyl, ethyl, propyl, 2-propyl or butyl esters) thereof.

Examples of specifically comtemplated dye precursors include compounds from the group comprising p-phenylene-diamine (PPD), p-toluylene-diamine (PTD), chloro-p-phenylene-diamine, p-aminophenol, o-aminophenol, 3,4-diaminotoluene, 2-methyl-1,4-diaminobenzene, 4-methyl-o-phenylenediamine, 2-methoxy-p-phenylenediamine, 2-chloro-1,4-diamino-benzene, 4-amino di-phenylamine, 1-amino-4-β-methoxyethylamino-benzene, 1-amino-4-bis-(β-hydroxyethyl)-amonibenzene, 1-3-diamino-benzene, 2-methyl-1,3-diamino-benzene, 2,4-diaminotoluene, 2,6-diaminopyridine, 1-hydroxy-2-amino-benzene, 1-hydroxy-3-amino-benzene, 1-methyl-2-hydroxy-4-amino-benzene, 1-methyl-2-hydroxy-4-β-hydroxyethylamino-benzene, 1-hydroxy-4-amino-ebnzene, 1-hydroxy-4-methylamino-benzene, 1-methoxy-2,4-diamino-benzene, 1-ethoxy-2,3-diamino-benzene, 1-β-hydroxyethyloxy-2,4-diamino-benzene, phenazines, such as 4,7-phenazinedicarboxylic acid, 2,7-phenazinedicarboxylic acid, 2-phenazinecarboxylic acid, 2,7-diaminophenazine, 2,8-diaminophenazine, 2,7-diamino-3,8-dimethoxyphenazine, 2,7-diamino-3-methoxyphenazine, 2,7-diamino 3-methoxyphenazine, 3-dimethyl 2,8-phenazinediamine, 2,2'-[(8-amino-7-methyl-2-phenazinyl)imino]bis-ethanol, 2,2'-[(8-amino-7-methoxy-2-phenazinyl)imino]bis-ethanol, 2,2'-[(8-amino-7-chloro-2-phenazinyl)imino]bis-ethanol, 2-[(8-amino-7-methyl-2-phenazinyl)amino]-ethanol, 2,2'-[(8-amino-2-phenazinyl)imino]bis-ethanol, 3-amino-7-(dimethylamino)-2,8-dimethyl-5-phenyl-chloride, 9-(diethylamino)-benzo[α]phenazine-1,5-diol, N-[8-(diethylamino)-2-phenazinyl]-methanesulfonamide, N-(8- methoxy-2-phenazinyl)-Methanesulfonamide, N,N,N',N'-tetramethyl-2,7-phenazinediamine, 3,7-dimethyl-2-phenazinamine, p-amino benzoic acids, such as p-amino benzoic acid ethyl, p-amino benzoic acid glycerid, p-amino benzoic acid isobutyl, p-dimethylamino benzoic acid amil, p-dimethylamino benzoic acid octyl, p-diethoxy amino benzoic amil, p-dipropoxy amino benzoic acid ethyl, acetylsalicylic acid, isatin derivatives, and 2,3-diamino benzoic acid.

(iii) Other Substrates for Laccases:

Laccases have proved to be very suitable for causing gelling of polysaccharides containing phenolic substituents (e.g. arabinoxylans from wheat or bran, or pectins from sugar beet and related plants) for food applications or for the preparation of highly water-absorbent materials (see, e.g. WO 96/03440). Similarly, laccases have proved to have very useful applications in the preparation of lignocellulose-based products from lignocellulosic material (e.g. wood pulp) and phenolic polysaccharides such as the arabinoxylans or pectins mentioned above (see, e.g., WO 96/03546).

It would thus be appropriate to provide a formulation of the invention comprising, for example, suitable levels of a laccase and a laccase substrate in the form of a phenolic polysaccharide. Such a ready-made, storage-stable formulation could be employed to advantage for applications as mentioned above.

MATERIALS AND METHODS

Materials

Enzymes:

Highly purified recombinant *Polyporus pinsitus* laccase (3525 LACU/ml) without any side activities and stored in 20 mM Tris-buffer at about pH 7.0 or 8.0 kept under at 4° C.

Pasteurized and un-pasteurized recombinant *Myceliophthora thermophila* laccase (aqueous concentrate produced by Novo Nordisk A/S, Bagsvaerd, Denmark; Mettler dry matter content 18.5% w/w; approximately 50 mg of pure laccase protein per gram of concentrate);

MES Buffer: (2-N-Morpholino-ethanesulfonic Acid (Sigma M-8250). pH is Adjusted to 5.5 Using 3N NaOH (Merck 1.06498).

Maleic acid, 1.0 M

| Maleic acid 37% paM *) 800380 | 23.2 g |
| Demineralized water, Milli Q | up to 200 ml |

*) pro analysi Merck 23.2 g Maleic acid is weighed in a weighing boat and added 150 ml water during continuously stirring. Stir until dissolved.

Transfer quantitatively the solution to a 200 mL volumetric flask and add up to the mark with water.

Tris buffer 1.0 M; Stock solution

| Tris[hydroxymethyl]aminomethane Sigma T-1378 | 121.1 g |
| Demineralized water, Milli Q | up to 1 l |

Tris buffer is weighed in a weighing boat and 800 ml of water is added during continuously stirring. Stir until dissolved.

Transfer quantitatively the solution to a 1 l volumetric flask and add up to the mark with water.

Tris buffer 25 mM; pH 7.50

| Tris buffer 1.0M | 25.0 ml |
| Maleic acid, 1.0M | 5.0 ml |
| Demineralized Water | up to 1 l | pH is adjusted to 7.50±0.05. Pour 50 ml Tris buffer 1.0 M (graduated glass) into a 1 l volumetric flask and add about 700 ml water. Now add 5 ml Maleic acid, 1 M. Adjust pH to 7.50±0.05 and add up to the mark with water. (pH may not be adjusted with HCl, because of the inhibiting effect on the Laccase-enzyme.)

Dilution media

| PEG 6000 paM 807491 | 25.0 g |
| Triton X-100, Sigma T-9284 | 5.0 g |
| Milli Q water | up to 0.5 l |

25.0 g PEG 6000 and 5.0 g Triton X-100 is weighed in a weighing boat and added 400 ml water during continuous stirring. Stir until dissolved.

Transfer quantitatively the solution to a 0.5 l volumetric flask and add up to the mark with water.

Syringaldazine, 0.56 mM; Stock solution

| Syringaldazine anh Sigma S-7896 | 10.0 mg |
| Ethanol 96% | 50 ml |

Syringaldazine is weighed in a 50 ml volumetric flask and added ethanol of 50 ml. Is stirred until dissolved (ap. 3 hours).

Syringaldazine, 0.28 mM; 48% ethanol

| Syringaldazine, 0.56 mM | 25.0 ml |
| Demineralized water, Milli Q | up to 50 ml |

25 ml syringaldazine, 0.56 mM (full pipette) is transferred to a 50 ml volumetric flask. Fill up to the mark with water. Check of the Reagent: Syringaldazine, 0.056 mM; 48% Ethanol:

| Syringaldazine, 0.28 mM | 2 ml |
| Ethanol, 96% | 4 ml |
| Demineralized water, Milli Q | up to 10 ml |

The solution should have an absorption of about 2.2 at 360 nm. measured against ethanol, 6%.

Ethanol. 6%

| Ethanol, 96% | 62.5 ml |
| Demineralized water, Milli Q | up to 1000 l |

62.5 ml ethanol, 96% (graduated glass) is transferred to a 1 l volumetric flask. Fill up to the mark with water.

Tris Na-buffer (20 mM in the formulation)

Glycine buffer

Phosphate buffer

Sorbitol syrup (60% dry matter in the formulation)
PEG 6,000 (30% or 60% dry matter in the formulation)
PEG 600 (30% or 60% dry matter in the formulation)
Proxel™
Ionic-water is used in the buffers
Triton X-100
Syringaldazin (Sigma S-7896)
Malein acid (Merck 800380)
Tris (SIGMA 7-9, T-1378)

Equipment:
<COBAS> FARA centrifugal analyzer, (Roche) Spectrophometer Shimadzu UV 2101 PC Methods Determination of Laccase Activity (LACU)

The LACU method can be used for determining the enzymatic activity of *Polyporus pinsitus* laccase and other laccases.

Laccase activity is determined from the oxidation of syringaldazin under aerobic conditions. The violet colour produced is photometered at 530 nm. The analytical conditions are 19 mM syringaldazin, 23.2 mM acetate buffer, pH 5.5, 30° C., 1 minute reaction time.

1 laccase unit (LACU) is the amount of enzyme that catalyses the conversion of 1.0 micromole syringaldazin per minute at these conditions.

Determination of Laccase Activity (LAMU)

The LAMU method is used for determining the activity of *Myceliophthora thermophila* laccase. 1 laccase unit (LAMU) is the amount of enzyme which catalyses the conversion of 1.0 micro mole syringaldazine per minute under the following analytical conditions.

Laccase catalyses under aerobic conditions the oxidation of syringaldazine forming tetramethoxy-azo-bis methylene quinone. The violet colour produced is photometered at 530 nm. The analytical conditions are in the reaction solution 16.5 microM syringaldazine, 20.3 mM Tris/malein acid buffer, pH 7.5, 30° C., 1 minute reaction time, the enzymatic activity range is between 0.0006–0.0028 LAMU/ml.

Detection limit (LOD): 0.005 LAMU/ml

Quantitative detection limit (LOQ): 0.01 LAMU/ml

Range of measurement: 0.01–0.044 LAMU/ml

The calculation is based on the changes in absorbance per minute, which is proportional with the enzymatic activity, linear with the reaction time and the enzyme concentration.

A stable, homogeneous sample is used as Level Control sample for determining the activity level. The Level Control sample is diluted to an expected activity of 0.025 LAMU/ml with diluent (50 g PEG6,000 in Milli-Q up to 1 liter). Samples are stored for 15 minutes before analysis. The analyzing of the unknown laccase test sample is performed e.g. on a <COBAS> FARA centrifugal analyzer.

<COBAS> FARA program

Operation T: The empty rotor turns around until the temperature in the cell cavity.

Operation P: 25 micro liter Level Control sample or test sample, 20 micro liter de-mineralized water (Milli-Q) and 325 micro liter buffer (i.e. 25 mM Tris/malein acid buffer, pH 7.5) is introduced into their respective cavity in the rotor.

Operation I: When the rotor accelerates the buffer and the sample is mixed in the cell.

Operation SR: 30 micro liter substrate (i.e. 0.56 mM Syringaldazine) is introduced into the smallest of the cavities in the rotor Operation A: When the rotor accelerates and centrifuges the substrate is mixed in the cell. 25 absorbance readings (5 seconds intervals) are made of both the Level Control sample, and the unknown laccase test sample. The $12^{th}$ to the $24^{th}$ absorbance readings (60–120 seconds) are used for calculating ΔABS/minutes. The activity is calculated on the basis of the <COBAS> FARA readings as [U/ml].

The following calculation are made:

$$LAMU/g = \frac{A \times Vol \times D}{W}$$

A=[U/ml] from <COBAS> FARA-reading means [LAMU/ml],

Vol=Tube used for sample dilution [ml]

D=Dilution of the dissolved sample [ml/ml]

W=Weight [g]

The activity is converted into activity by the following calculations:

$$A = F \times \Delta ABS/min$$

ΔABS/min=Change in absorbance per minute at 530 nm, calculated by <COBAS> FARA.

$$F = \frac{V}{v \times E \times b}$$

$$F = \frac{0.400 \times 10^{-3} \times 10^{-3*)}}{0.025 \times 10^{-3} \times 0.065 \times 1.6}$$

$$F = 0.154^{**)}$$

*) $10^{-3}$ = Conversion of micro mole/liter to micro mole/ml.

**) at 1.6 cm sample path length

V=Total volume in reaction mixture in <COBAS> FARA [L]

v=Test volume in reaction mixture [L]

E=micro molar extinction coefficient at 530 nm [0.065/1 cm sample path length, (Bauer, R. et al.,(1971), Anal. Chem. 43(3) 421–5)].

b=sample path length (cm). Total volume, V, is 400 ml corresponding to the sample path length in the cell of 1.6 cm, b.

EXAMPLES

Example 1

Storage-stability of *M. thermophila* Laccase and *Polyporus pinsitus* Laccase in Buffer at the pH Optimum (without polyalcohol(s)

*M. thermophila* laccase and *Polyporus pinsitus* laccase were stored at their pH optima (i.e. pH 6.5 and 5.5, respectively) at 40° C. for 16 days.

The *M. thermophila* laccase was dissolved in 25 mM Tris/HCl buffer and the pH was adjusted to pH 6.5 to make out an activity of 1000 LAMU/ml. The *Polyporus pinsitus* laccase was dissolved in 25 mM MES buffer and pH adjusted to pH 5.5 to make out an activity of 1000 LACU/ml.

The dissolved enzymes were placed at 4°, and 40° C. respectively and samples were taken out to be analyzed at the following intervals: 24 hours, 3 days, 7 days and 16 days.

Figure 5:
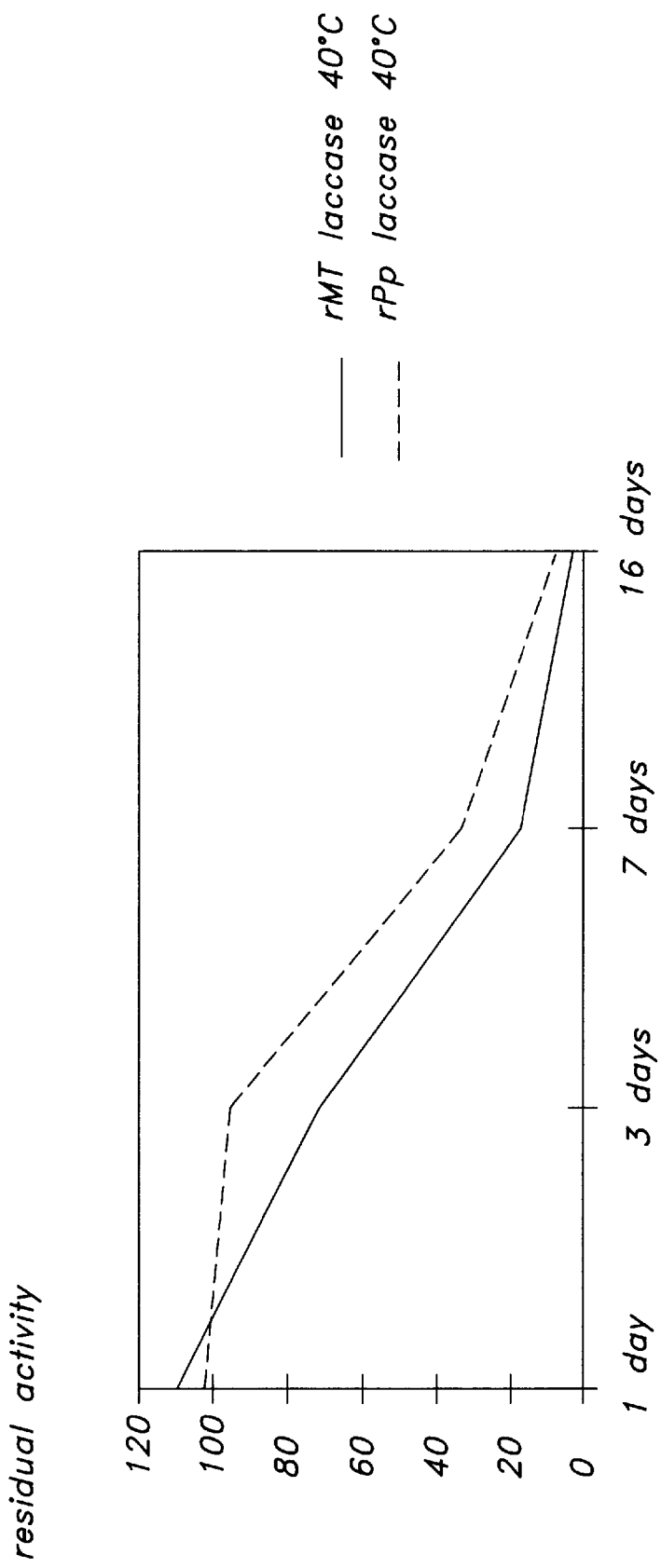
FIG. 5 shows the stability of *Myceliophthora thermophila* laccase and *Polyporus pinsitus* laccase in buffer measured as the residual activity during a period from 1 to 16 days at 40° C.

The relative residual activity is related to corresponding formulations kept at 4° C. (blind), i.e. the residual activity at 4° C. is considered to be 100% residual activity. The result of the test can be seen in FIG. 5.

After 16 days the relative residual activity of the *M. thermophila* laccase and *Polyporus pinsitus* laccase at 40° C. the residual activity were 3% and 8%, respectively.

Example 2

Storage-stability of *Polyporus pinsitus* Laccase (14 days)

The storage-stability of liquid formulations comprising a highly purified *Polyporus pinsitus* laccase (10 LACU/g) and two different polyalcohols were tested at pH 7.0, 8.0 and 9.0.

The samples specified in Table 1 and Table 2 were prepared and stored for 14 days. The residual laccase activity after storage were calculated on the basis of the laccase activity at 4° C. samples under corresponding conditions.

TABLE 1

| Formulation | 4° C. LACU/g | 40° C. LACU/g | Residual activity after 14 days |
|---|---|---|---|
| 60% Sorbitol pH 7.0 | 9.0 | 5.9 | 65% |
| 60% Sorbitol pH 8.0 | 9.7 | 7.9 | 82% |
| 60% Sorbitol pH 9.0 | 9.8 | 9.5 | 96% |

TABLE 2

| Formulation | 4° C. LACU/g | 40° C. LACU/g | Residual activity after 14 days |
|---|---|---|---|
| 60% PEG 6,000 pH 7.0 | 7.2 | 7.0 | 97% |
| 60% PEG 6,000 pH 8.0 | 8.7 | 7.6 | 88% |
| 60% PEG 6,000 pH 9.0 | 9.8 | 9.7 | 100% |

It can be seen from the Table 1 and Table 2 that an improved storage-stability is obtained in the presence of a polyalcohol.

Example 3

Storage-stability of *Polyporus pinsitus* Laccase (4 weeks)

The test described in Example 1 was repeated for PEG6,000 at 40° C., expect that the storage period was 4 week.

TABLE 3

| Formulation | 4° C. LACU/g | 40° C. LACU/g | Residual activity after 4 weeks |
|---|---|---|---|
| 60% PEG 6,000 pH 7.0 | 7.5 | 2.2 | 29% |
| 60% PEG 6,000 pH 8.0 | 8.4 | 4.2 | 49% |
| 60% PEG 6,000 pH 9.0 | 8.8 | 5.7 | 65% |

As can be see from Table 3, after 4 weeks a substantial residual activity is retained at higher pH values.

Example 4

Storage-stability of *Myceliophthora thermophila* Laccase

The storage stability of a liquid solution comprising recombinant *Myceliophthora thermophila* laccase (120 LAMU/g) and 30% or 60% PEG 6,000 and PEG 600 were tested at pH 7.0, 8.0 and 9.0.

The following ingredients were used in the test:
AI: PEG 6000 as 30 or 60%
AII: PEG 600 as 30 or 60%
B: pH 8.0 or 9.0 with 20 mM Tris/malein buffer.

Storage:
The formulations were stored in 20 ml sample containers with rubber sealed lids. Before closing the lids the containers were vacuumed and the vacuum was broken with Argon. In this way the formulations are stored under an inert gas atmosphere.

Storage Temperatures:
4, 25 and 40° C. Sampling periods: 1, 2 and 4 weeks.

Table 4 shows result of the storage-stability tests of formulations comprising PEG 6,000:

TABLE 4

PEG 6,000 Formulations

| Formulation | Weeks | 25° C. % residual activity | 40° C. % residual activity |
|---|---|---|---|
| 30% PEG pH 8.0 | 1 | 92.0% | 76.0% |
| 30% PEG pH 8.0 | 2 | 92.8% | 75.2% |
| 30% PEG pH 8.0 | 4 | 114.4% | 37.8% |
| 60% PEG pH 8.0 | 1 | 94.8% | 74.9% |
| 60% PEG pH 8.0 | 2 | 85.0% | 59.2% |
| 60% PEG pH 8.0 | 4 | 103.6% | 63.7% |
| 30% PEG pH 9.0 | 1 | 92.8% | 90.7% |
| 30% PEG pH 9.0 | 2 | 100.4% | 86.1% |
| 30% PEG pH 9.0 | 4 | 93.6% | 78.2% |
| 60% PEG pH 9.0 | 1 | 108.5% | 86.2% |
| 60% PEG pH 9.0 | 2 | 78.5% | 69.2% |
| 60% PEG pH 9.0 | 4 | 82.9% | 47.5% |

The result of the storage-stability tests of the formulations comprising PEG600 is shown in Table 5.

TABLE 5

PEG 600 Formulations

| Formulation | Weeks | 25° C. % residual activity | 40° C. % residual activity |
|---|---|---|---|
| 30% PEG pH 8.0 | 1 | 83.0% | 9.9% |
| 60% PEG pH 8.0 | 1 | 86.3% | 75.2% |
| 60% PEG pH 8.0 | 2 | 93.6% | 78.5% |
| 60% PEG pH 8.0 | 4 | 76.5% | 45.0% |
| 30% PEG pH 9.0 | 1 | 89.0% | 11.3% |
| 60% PEG pH 9.0 | 1 | 89.0% | 89.2% |
| 60% PEG pH 9.0 | 2 | 88.6% | 92.7% |
| 60% PEG pH 9.0 | 4 | 84.9% | 42.6% |

As can be seen from the Table 4 and Table 5 liquid formulations comprising *Myceliophthora thermophila* laccase and PEG6,000 or PEG600, respectively, as the polyalcohol have improved storage-stability. Further, from FIG. 1 it can be seen that a substantial residual enzymatic activity is maintained for the formulation comprising 30% PEG6,000 at pH 9.0.

Example 5

Storage-stability of *Myceliophthora thermophila* Laccase

The storage-stability of liquid formulations comprising *Myceliophthora thermophila* laccase, mono propylene glycol (MPG) or glycerol and a buffer at pH 9 and 10.

The following formulations shown in Table 6 were tested, all of them comprising
● 320–370 LAMU/g
● 2% of Proxel™

TABLE 6

| No. | Stabilizer | pH | Buffer |
|---|---|---|---|
| 1 | 20% MPG | 9 | 0.05M borax |
| 2 | 20% MPG | 9 | 0.05M phosphate |
| 3 | 20% MPG | 9 | 0.05M tris/malein |
| 4 | 20% MPG | 10 | 0.05M glycine |
| 5 | 20% MPG | 10 | 0.05M borax |
| 6 | 20% glycerol | 9 | 0.05M tris/malein |

TABLE 6-continued

| No. | Stabilizer | pH | Buffer |
|---|---|---|---|
| 7 | 30% MPG | 9 | 0.05M tris/malein |
| 8 | 20% MPG | 9 | NaOH |
| 9* | 20% MPG | 9 | 0.05M tris/malein |

*Formulation no. 9 is based on the pasteurized raw material.
Formulation no. 1–8 are based on the untreated raw material.

Figure 2:
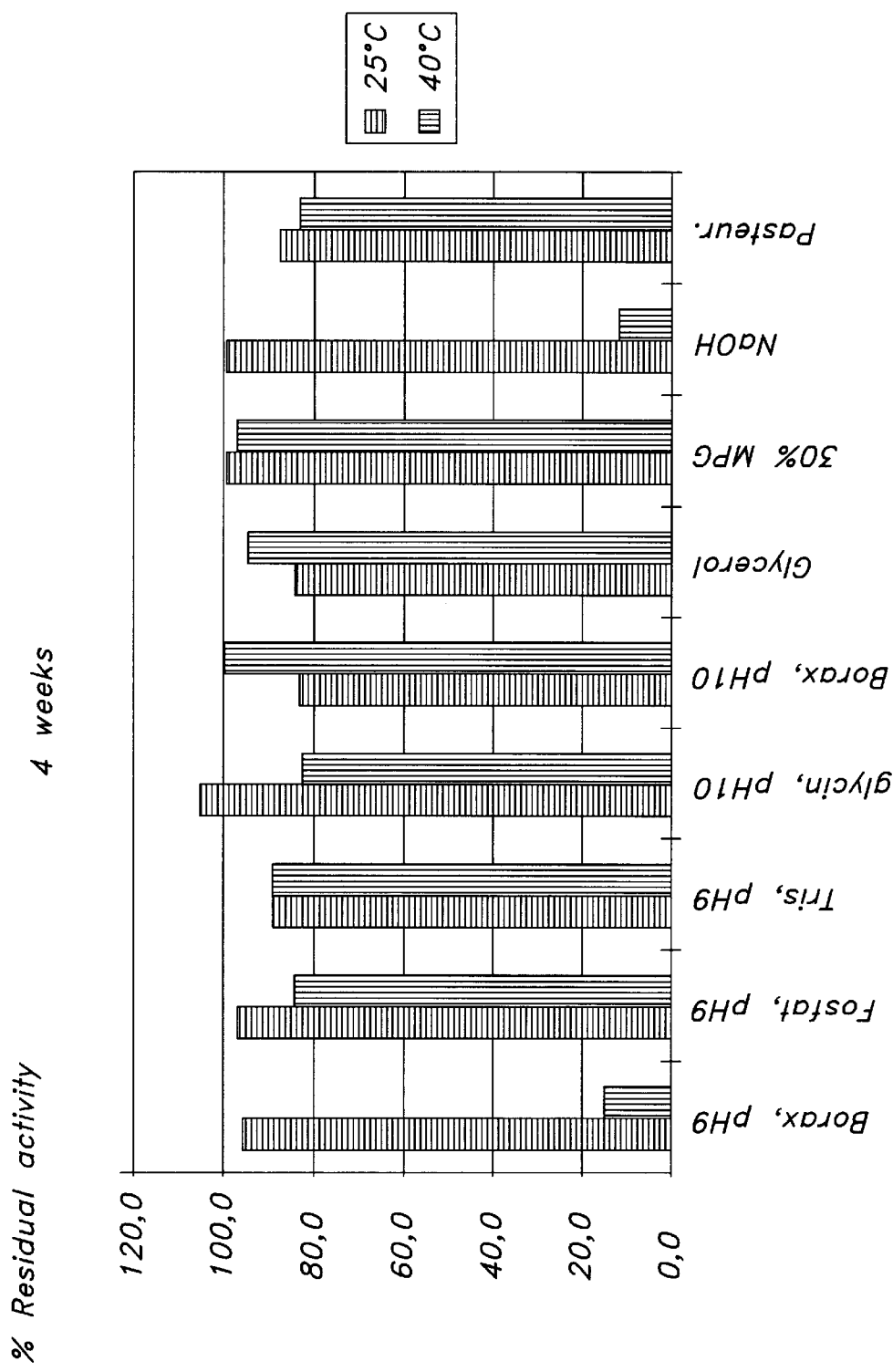
FIG. 2 shows the percentage residual activity of liquid formulations comprising *Myceliophthora thermophila* laccase and a polyalcohol and different buffers.

Results:

The residual activity after 4 weeks storage is shown in FIG. 2.

All activities are calculated as percentage of the activity of the average of reference samples stored at 40° C. within the same period (average based on 0, 2 and 4 weeks results).

The results show that all formulations maintained more than 80% of the activity after 4 weeks storage at 25° C. After storage at 40° C., all formulations except the formation comprising borax pH 9 and the blind (the NaOH formulation in which pH is adjusted to 9 and no other buffer is added), also maintain at least 80% of the initial activity.

Example 6
The Effect of Different Parameters on the Storage-stability

The influence on the residual enzymatic activity of
■ replacing MPG with glycerol, and
■ increasing the amount of MPG, and
■ applying pasteurized raw material, were tested.

The following formulations (shown in Table 7) were tested, all of them comprising
● 320–370 LAMU/g
● 0.2% of Proxel z1

TABLE 7

| No. | Stabilizer | pH | Buffer |
|---|---|---|---|
| 1 | 20% MPG | 9 | 0.05M Tris/malein |
| 2 | 20% Glycerol | 9 | 0.05M Tris/malein |
| 3 | 30% MPG | 9 | 0.05M Tris/malein |
| 4* | 20% MPG | 9 | 0,05M Tris/malein |

*Formulation 4 is based on pasteurized raw material

Figure 3:
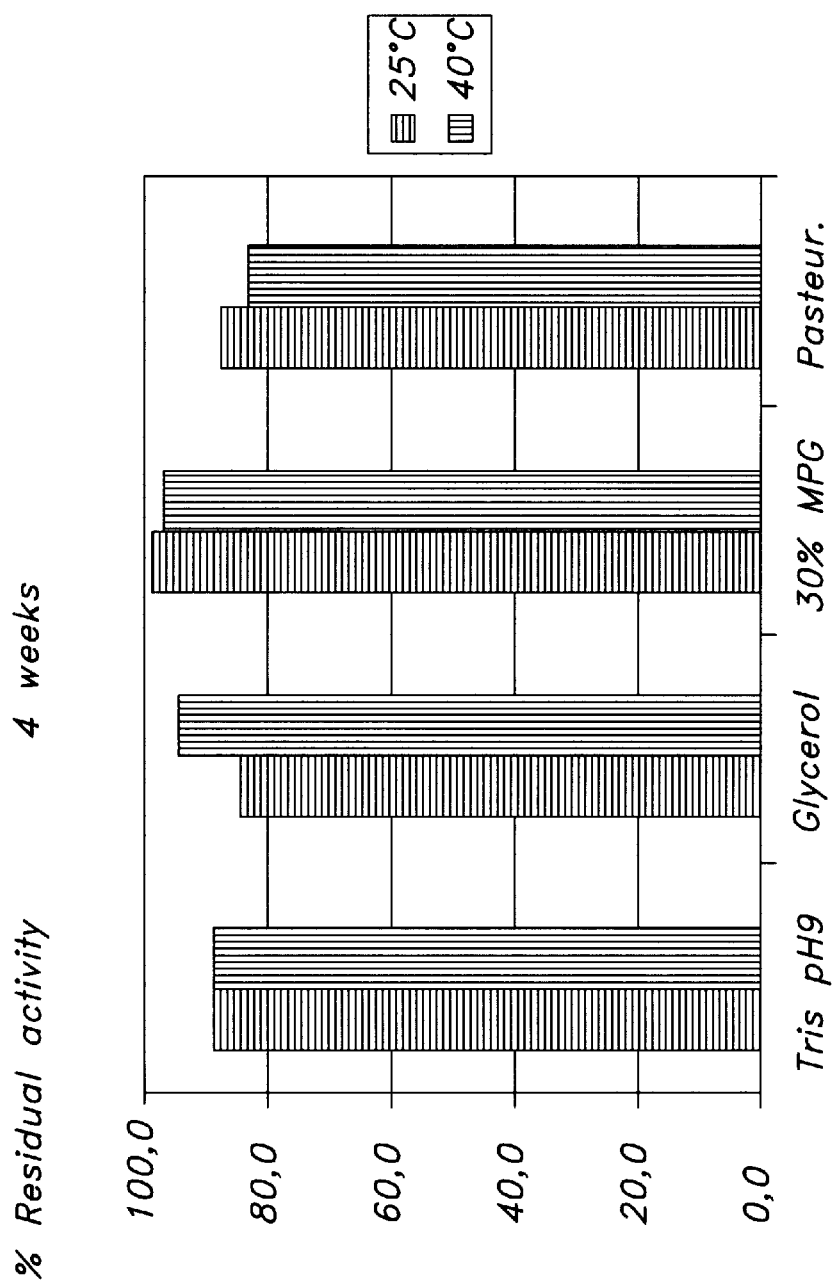
FIG. 3 shows the effect of the polyalcohol and pasteurization of the *Myceliophthora thermophila* laccase raw material.

Result:

The result of the test is displayed in FIG. 3. It can be seen than all liquid formulation comprising *Myceliophtora thermophila* laccase has more than 80% residual activity after 4 weeks.

Example 7
Storage-stability of *M. thermophila* Laccase at Different pHs

The residual activity of *Myceliophthora thermophila* laccase (250 LAMU/g) in a liquid formulation comprising in 0.25 M Glycine buffer comprising 10% MPG and 0.2% Proxel™ was tested.

The result of the test can be seen from FIG. 4. The laccase is most stable at the pH 9.0 where 93% and 84% activity is maintained after 4 weeks storage at 25° C. and 40° C. respectively.

Example 8

Storage of *M. thermophila* Laccase for 21 Weeks at 40° C.

*M. thermophila* laccase were stored for 21 weeks at 40° C. (pH 9.0) in liquid formulation 1 and 2, respectively.
Formulation 1:
250 LAMU/g (or 3.1 mg enzyme protein per g)
10% w/w propylene glycol
0.2% Proxel™
0.25 M Glycine buffer (from a 2 M Glycine buffer, in which pH is adjusted to pH 9.0 with 4 N NaOH)
All ingredients were stirred thoroughly, pH is adjusted to pH 9.0±0.1 and demineralized water is added to final volume.
Formulation 2:
250 LAMU/g (or 3.1 mg enzyme protein per g)
10 w/w propylene glycol
3% w/w glucose
0.2% Proxel™
0.25 M Glycine buffer (from a 2 M Glycine buffer, in which pH is adjusted to pH 9.0 with 4 N NaOH)
All ingredients were stirred thoroughly, pH is adjusted to pH 9.0±0.1 and demineralized water is added to final volume.

Figure 6:
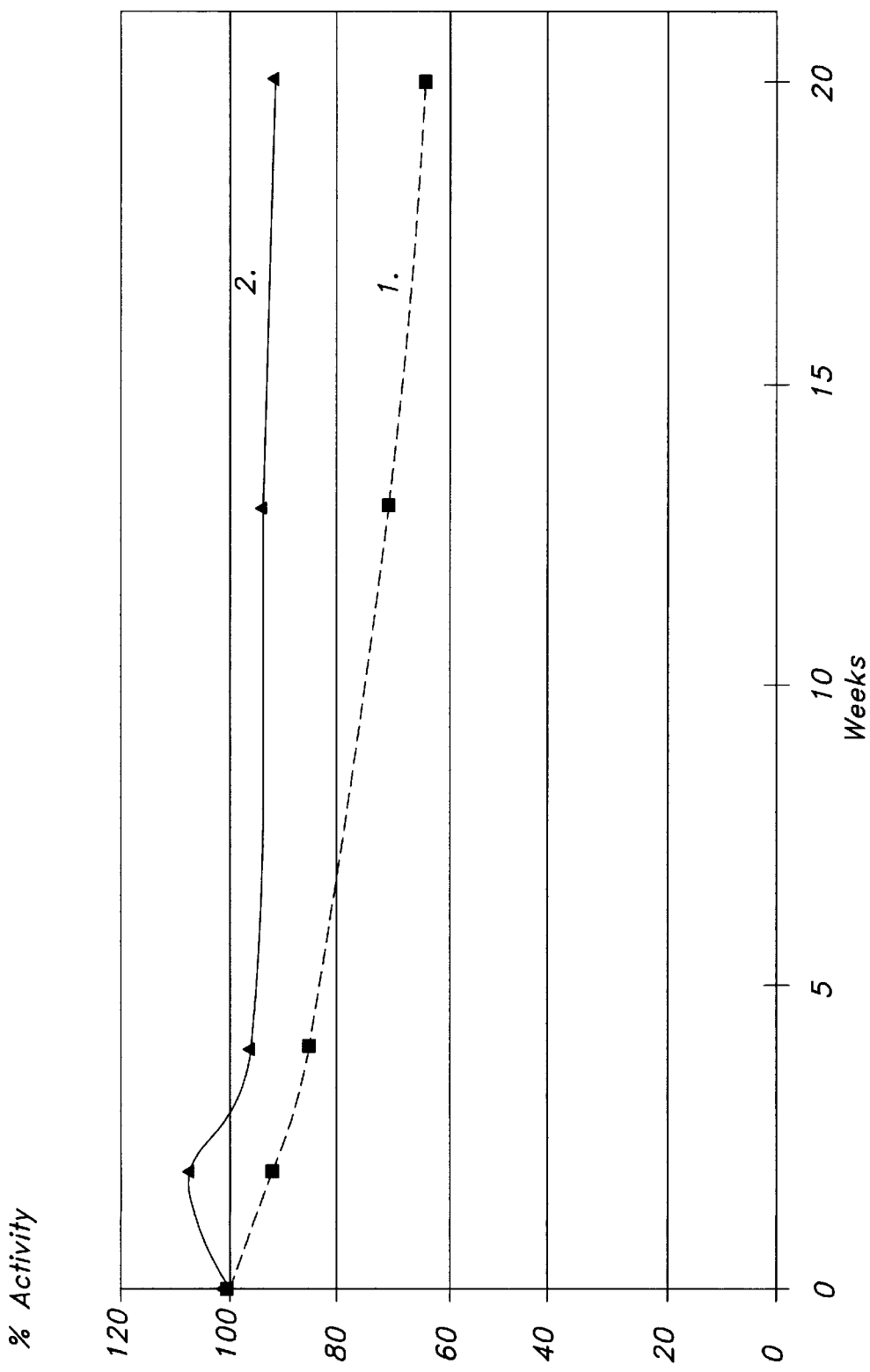
FIG. 6 shows long term storage stability of *Myceliophthora thermophila* laccase for a period of 21 weeks at 40° C. in a liquid formulation comprising 1) 10% w/w propylene glycol and 2) the combination of 10% w/w propylene glycol and 3% w/w glucose.

The result of the test is displayed in FIG. 6. The relative residual activity is related to corresponding formulations kept at 4° C. (blinds), i.e. the residual activity at 4° C. is considered to be 100% residual activity.

As can be seen from FIG. 6, after 20 weeks storage at 40° C. the residual activity is around 65% in Formulation 1 (10% w/w propylene glycol) and around 90% in Formulation 2 (10% w/w propylene glycol+3% w/w glucose).

What is claimed is:

1. A storage-stable liquid laccase formulation comprising
    (i) a laccase derived from Polyporus and
    (ii) at least one polyalcohol at a concentration from about 5 to about 75% of said formulations;
    wherein said formulation has a pH at least between about 1 and 5 pH units more alkaline than the pH optimum of the laccase, when said pH optimum is measured using syringaldazine as a substrate; and
    wherein storage of the formulation for 14 days at 40° C. results in maintenance of at least 30% of the enzymatic activity of the laccase in said formulation as compared with the enzymatic activity of the laccase in an identical formulation stored for 14 days at 4° C.

2. The liquid formulation according to claims 1 wherein the said polyalcohol is a polymer or a monomer thereof, or a saccharide which is a mono-, di-, oligo- or polysaccharide.

3. The liquid formulation according to claim 2 wherein the polyalcohol is a polyalkylene oxide (PAO), poly-vinyl alcohol (PVA), polyethylene-co-maleic acid anhydride, polystyrene-co-malic acid anhydrid, dextrans celluloses, hydrolysates of chitosan, starches glycogen, glycerol, sorbitol, agaroses and derivates thereof, guar gum, pullulan, inulin, xanthan gum, carrageenan, pectin, alginic acid hydrolysates, bio-polymers, sorbitol, glucose, mannose, galactose, arabinose, gulose, xylose, threose, sorbose, fructose, glycerol, maltose cellobiose, sucrose, amylose, amylopectin, or mono propylene glycol (MPG).

4. The liquid formulation according to claim 2, wherein the polyalcohol is at least one of a polymer and a saccharide.

5. The liquid formulation according to claim 2 wherein the polymer is a polyalkylene oxide (PAO).

6. The liquid formulation according to claim 2 wherein the saccharide is glucose.

7. The liquid formulation according to claim 4, wherein the polymer and/or the saccharide has a molecular weight of from 200 da to 8,000 da.

8. The formulation according to of claim 1, wherein a pH regulating agent is added to adjust the pH of the liquid formulation.

9. The formulation according to claim 1, wherein the pH of the formulation is between 7 to 12.

10. The formulation according to claim 1, further comprising anti-microbial agents, dispersing agents and/or viscosity-regulating agents.

11. The formulation according to claim 1 wherein the liquid formulation is a water-based formulation.

12. A method for improving the storage-stability of a laccase derived from Polyporus, said method comprising storing the laccase in a formulation comprising 5–75% of a polyalcohol at a pH which is 1 to 5.5 pH units more alkaline than the pH optimum of the laccase when said pH optimum is measured using syringaldazine as a substrate, wherein storage of the formulation for 14 days at 40° C. results in maintenance of at least 30% of the enzymatic activity of the laccase in said formulation as compared with the enzymatic activity of the laccase in an identical formulation stored for 14 days at 4° C.

13. The liquid formulation according to claim 3, wherein the polyalkylene oxide is a polyalkylene glycol (PAG) comprising polymethylene glycols (PMG), polyethylene glycols (PEG), methoxypolyethylene glycols (mPEG) and polypropylene glycols.

14. The liquid formulation according to claim 3, wherein the dextrans includes carboxy-methyl dextrans.

15. The liquid formulation according to claim 3, wherein the celluloses include methylcellulose, carboxymethylcellulose, ethylcellulose, hydroxyethylcellulose carboxyethylcellulose and hydroxypropylcellulose.

16. The liquid formulation according to claim 3, wherein the starches include hydroxyethyl-starches and hydroxypropyl starches.

17. The liquid formulation according to claim 5, wherein the polyalkylene oxide (PAO) is a polyalkylene glycol (PAG).

18. The liquid formulation according to claim 17, wherein the polyalkylene glycol (PAG) is propylene glycol.

19. The liquid formulation according to claim 7, wherein the molecular weight is from 400 to 7,000 da.

20. The liquid formulation according to claim 19, wherein the molecular weight is 6,000 da.

21. The formulation according to claim 1, wherein the polyalcohol constitutes from 10 to 60% of the liquid formulation.

22. The formulation according to claim 21, wherein the polyalcohol constitutes from 20 to 50% of the liquid formulation.

23. The formulation according to claim 9, wherein the pH is from 7.5 to 11.

24. The formulation according to claim 23, wherein the pH is between 6.5 and 9.5.

* * * * *